(12) United States Patent
Kimura et al.

(10) Patent No.: US 10,792,302 B2
(45) Date of Patent: Oct. 6, 2020

(54) COMPOSITION FOR PREVENTING OR TREATING METABOLISM DISORDERS COMPRISING LEUCONOSTOC MESENTEROIDES-PRODUCING EXOPOLYSACCHARIDE AS ACTIVE INGREDIENT

(71) Applicant: Noster Inc., Muko-shi, Kyoto (JP)

(72) Inventors: Ikuo Kimura, Kunitachi (JP); Kenji Yamamoto, Otsu (JP); Keiko Hisa, Muko (JP)

(73) Assignee: Noster Inc., Muko (JP)

(*) Notice: Subject to any disclaimer, the term of this patent is extended or adjusted under 35 U.S.C. 154(b) by 87 days.

(21) Appl. No.: 16/079,498

(22) PCT Filed: Feb. 24, 2017

(86) PCT No.: PCT/JP2017/007137
§ 371 (c)(1),
(2) Date: Aug. 23, 2018

(87) PCT Pub. No.: WO2017/146213
PCT Pub. Date: Aug. 31, 2017

(65) Prior Publication Data
US 2019/0099438 A1 Apr. 4, 2019

(30) Foreign Application Priority Data

Feb. 24, 2016 (JP) .................................. 2016-032889
Jul. 7, 2016 (JP) .................................. 2016-134997

(51) Int. Cl.
| A61K 31/715 | (2006.01) |
| A61K 35/744 | (2015.01) |
| A23L 33/10 | (2016.01) |
| A23K 10/16 | (2016.01) |
| A23K 20/163 | (2016.01) |
| A61P 1/16 | (2006.01) |
| A61P 3/04 | (2006.01) |
| A61P 3/06 | (2006.01) |
| A61P 3/10 | (2006.01) |
| A23L 29/269 | (2016.01) |
| A23L 33/135 | (2016.01) |

(52) U.S. Cl.
CPC ............ *A61K 31/715* (2013.01); *A23K 10/16* (2016.05); *A23K 20/163* (2016.05); *A23L 33/10* (2016.08); *A61K 35/744* (2013.01); *A61P 1/16* (2018.01); *A61P 3/04* (2018.01); *A61P 3/06* (2018.01); *A61P 3/10* (2018.01); *A23L 29/273* (2016.08); *A23L 33/135* (2016.08)

(58) Field of Classification Search
None
See application file for complete search history.

(56) References Cited

U.S. PATENT DOCUMENTS

| 8,816,067 B2* | 8/2014 | Naeye .................. A61K 31/733 536/123.12 |
| 2010/0284972 A1 | 11/2010 | Naeye et al. |
| 2011/0311502 A1 | 12/2011 | Sugiyama et al. |
| 2014/0079676 A1 | 3/2014 | Olmstead |
| 2016/0229925 A1 | 8/2016 | Yamamoto et al. |

FOREIGN PATENT DOCUMENTS

| JP | 2008-179595 A | 8/2008 |
| JP | 2010-200611 A | 9/2010 |
| JP | 2012-526145 A | 10/2012 |
| WO | WO 2001/088095 A1 | 11/2001 |
| WO | WO 2015/041299 A1 | 3/2015 |

OTHER PUBLICATIONS

Russ-Maciedo, P. et al., Intl Dairy J. 2002, vol. 12, pp. 163-171.*
Fukuda et al., "Exopolysaccharides from dairy lactic acid bacteria," *Bulletin of Dairy Technical Association*, 60: 66-92 (2010), English abstract and Int'l Search Report in PCT/JP2017/007137 (dated Apr. 4, 2017).
Fukuda et al., "Nyusankin no Saibogai Tato," *Bulletin of Applied Glycoscience*, 5(1): 31-37 (2015), Int'l Search Report in PCT/JP2017/007137 (dated Apr. 4, 2017).
Kimura et al., "Short-chain fatty acids and ketones directly regulate sympathetic nervous system via G protein-coupled receptor 41 (GPR41)," *Proc. Natl. Acad. Sci. U.S.A.*, 108(19): 8030-8035 (2011).
Kimura et al., "The gut microbiota suppresses insulin-medicated fat accumulation via the short-chain fatty acid receptor GPR43," *Nat. Commun.*, 4: 1829 (2013).
Miyamoto et al., "Metabolic benefits by *Leuconostoc mesenteroides* NTM048 derived exopolysaccharides," *Journal of Japan Society for Lactic Acid Bacteria*, 27(2): 133 (Jun. 26, 2016), English translation.
Ruas-Madiedo et al., "An overview of the functionality of exopolysaccharides produced by lactic acid bacteria," *International Dairy Journal*, 12(2-3): 163-171 (2002).
Turnbaugh et al., "An obesity-associated gut microbiome with increased capacity for energy harvest," *Nature*, 444(7122): 1027-1031 (2006).

(Continued)

*Primary Examiner* — Heidi Reese
(74) *Attorney, Agent, or Firm* — Leydig, Voit & Mayer, Ltd.

(57) ABSTRACT

The present invention provides a prophylactic or therapeutic composition for a metabolic disorder, a composition for amplifying the amount of short-chain fatty acid in the intestine, or a composition for decreasing a ratio of bacteria belonging to the Firmicutes to bacteria belonging to the Bacteroidetes in the intestine, each containing an exopolysaccharide produced by *Leuconostoc mesenteroides*, and further, a food, a pharmaceutical product, a feed and the like containing the composition.

4 Claims, 8 Drawing Sheets

Specification includes a Sequence Listing.

(56) References Cited

OTHER PUBLICATIONS

Japanese Patent Office, International Search Report in International Patent Application No. PCT/JP2017/007137 (dated Apr. 4, 2017), English translation.
European Patent Office, Extended European Search Report in European Patent Application No. 17756647 (dated Oct. 16, 2019).

* cited by examiner n = 8-10
** $p < 0.01$ and * $p < 0.05$ vs Cellulose n = 4-5
** $p < 0.01$ vs Cellulose
$p < 0.05$ vs 10% NTM048 EPS

COMPOSITION FOR PREVENTING OR TREATING METABOLISM DISORDERS COMPRISING LEUCONOSTOC MESENTEROIDES-PRODUCING EXOPOLYSACCHARIDE AS ACTIVE INGREDIENT

CROSS-REFERENCE TO RELATED APPLICATIONS

This patent application is the U.S. national phase of International Patent Application No. PCT/JP20157/007137, filed Feb. 24, 2017, which claims the benefit of Japanese Patent Application No. 2016-032889, filed on Feb. 24, 2016, and Japanese Patent Application No. 2016-134997, filed on Jul. 7, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,161 bytes ASCII (Text) file named "740310SequenceListing.txt," created Aug. 17, 2018.

TECHNICAL FIELD

The present invention relates to a prophylactic or therapeutic composition for metabolic disorder or a composition for amplifying the amount of short-chain fatty acid (SCFA) in the intestine, each comprising an exopolysaccharide (hereinafter to be also referred to as EPS) produced by *Leuconostoc mesenteroides*, particularly *Leuconostoc mesenteroides* NTM048 strain deposited under accession number NITE BP-1519 or a mutant strain thereof, as an active ingredient. *Leuconostoc mesenteroides* NTM048 strain was deposited under accession number NITE BP-1519 on Jan. 25, 2013 at the National Institute of Technology and Evaluation, Patent Microorganisms Depositary (NPMD), 2-5-8 Kazusakamatari, Kisarazu-shi, Chiba-ken, 292-0818, Japan. More particularly, the present invention relates to a prophylactic or therapeutic composition for, for example, obesity, diabetes, impaired glucose tolerance, hyperinsulinemia, hyperlipemia, fatty liver or the like, a composition for amplifying the amount of short-chain fatty acid in the intestine or a composition for decreasing the ratio of bacteria belonging to the Firmicutes to bacteria belonging to the Bacteroidetes in the intestine, each utilizing the physiological functions of exopolysaccharide produced by *Leuconostoc mesenteroides* (a suppressive action on body weight gain, a suppressive action on adipose tissue increase, a suppressive action on increase in blood glucose level, an increasing action on the amount of short chain fatty acid in the intestine and a decreasing action on the ratio of bacteria belonging to the Firmicutes to bacteria belonging to the Bacteroidetes in the intestine). Also, the present invention relates to the composition serving as a food, a pharmaceutical product, a feed or the like.

BACKGROUND ART

In recent years, metabolic syndrome accompanied by obesity due to overeating, lack of exercise and the like, particularly accumulation of visceral fat, has become a social problem. Metabolic syndrome refers to a state in which at least two out of hyperglycemia, hypertension and hyperlipemia are combined with visceral fat type obesity and arteriosclerosis is easily caused. Among Japanese people of 40 to 74 years old, one out of two men and one out of five females are estimated to have metabolic syndrome or are people at risk of developing same. Thus, the importance of optimizing the calorie intake by diet therapy has been proposed for the prevention and resolution of the progress of lipid accumulation in metabolic syndrome.

In addition, it has recently been clarified that changes in intestinal microflora are involved in host energy regulation, nutritional intake, immune function, and the like, and directly affect obesity and diseases such as diabetes and the like. The present inventors previously reported that short-chain fatty acid, which is a fermented product by enteric bacterium, regulates sympathetic nerve via GPR41 and regulates energy consumption (non-patent document 1), short-chain fatty acid suppresses insulin signal via GPR43 of adipocyte, thereby suppressing glucose uptake, and consequently suppresses fat accumulation, and the decrease in insulin sensitivity of the whole body is suppressed by suppressing obesity due to fat accumulation (non-patent document 2).

However, to increase the amount of short-chain fatty acid in the intestine for the purpose of preventing and treating metabolic syndrome, the intestinal microflora needs to be controlled appropriately. To do so, it is necessary to improve the lifestyle including eating habits over the long term, and a simpler and more efficient method for amplifying the amount of short-chain fatty acid in the intestine has been desired.

Document List

Non-Patent Document non-patent document 1: I. Kimura, et al., "Short-chain fatty acids and ketones directly regulate sympathetic nervous system via GPR41", Proc Natl Acad Sci USA. 108, 8030-8035 (2011).

non-patent document 2: I. Kimura, et al., "The gut microbiota suppresses insulin-mediated fat accumulation via the short-chain fatty acid receptor GPR43", Nature Communications 4, 1829 (2013).

SUMMARY OF THE INVENTION

Problems to be Solved by the Invention

An object of the present invention is to provide a prophylactic or therapeutic composition for metabolic disorder or a composition for amplifying the amount of short-chain fatty acid in the intestine, by increasing the amount of short-chain fatty acid in the intestine and the like.

Means of Solving the Problems

The present inventors have conducted intensive studies in view of the above-mentioned problems and found that exopolysaccharides produced by *Leuconostoc mesenteroides* have a suppressive action on body weight gain, a suppressive action on adipose tissue increase, a suppressive action on blood glucose level increase, an increasing action on the amount of short-chain fatty acid in the intestine, and a decreasing action on the ratio of bacteria belonging to the Firmicutes to bacteria belonging to the Bacteroidetes in the intestine, which are conventionally unknown physiological functions.

The present invention has been completed based on the above-mentioned findings.

That is, the present invention provides the following:

[1] A prophylactic or therapeutic composition for a metabolic disorder, comprising an exopolysaccharide produced by *Leuconostoc mesenteroides* as an active ingredient.

[2] The composition of [1], wherein the *Leuconostoc mesenteroides* is *Leuconostoc mesenteroides* NTM048 strain deposited under accession number NITE BP-1519 or a mutant strain thereof.

[3] The composition of [1] or [2], wherein the metabolic disorder is at least one kind selected from the group consisting of obesity, diabetes, impaired glucose tolerance, hyperinsulinemia, hyperlipemia, increase in adipose tissue and fatty liver.

[4] A composition for amplifying the amount of short-chain fatty acid in the intestine, comprising an exopolysaccharide produced by *Leuconostoc mesenteroides* as an active ingredient.

[5] The composition of [4], wherein the *Leuconostoc mesenteroides* is *Leuconostoc mesenteroides* NTM048 strain deposited under accession number NITE BP-1519 or a mutant strain thereof.

[6] The composition of [4] or [5], wherein the short-chain fatty acid is at least one kind selected from the group consisting of lactic acid, acetic acid, propionic acid and butyric acid.

[7] A composition for decreasing a ratio of bacteria belonging to the Firmicutes to bacteria belonging to the Bacteroidetes in the intestine, comprising an exopolysaccharide produced by *Leuconostoc mesenteroides* as an active ingredient.

[8] The composition of [7], wherein the *Leuconostoc mesenteroides* is *Leuconostoc mesenteroides* NTM048 strain deposited under accession number NITE BP-1519 or a mutant strain thereof.

[9] The composition of any one of [1] to [8] that is a food or food additive.

[10] The composition of any one of [1] to [8] that is a pharmaceutical product.

[11] The composition of any one of [1] to [8] that is a feed or a feed additive.

[12] A method for preventing or treating a metabolic disorder, comprising administering an effective amount of an exopolysaccharide produced by *Leuconostoc mesenteroides* to a subject.

[13] The method of [12], wherein the *Leuconostoc mesenteroides* is *Leuconostoc mesenteroides* NTM048 strain deposited under accession number NITE BP-1519 or a mutant strain thereof.

[14] The method of [12] or [13], wherein the metabolic disorder is at least one kind selected from the group consisting of obesity, diabetes, impaired glucose tolerance, hyperinsulinemia, hyperlipemia, increase in adipose tissue and fatty liver.

[15] A method for amplifying the amount of short-chain fatty acid in the intestine, comprising administering an effective amount of an exopolysaccharide produced by *Leuconostoc mesenteroides* to a subject.

[16] The method of [15], wherein the *Leuconostoc mesenteroides* is *Leuconostoc mesenteroides* NTM048 strain deposited under accession number NITE BP-1519 or a mutant strain thereof.

[17] The method of [15] or [16], wherein the short-chain fatty acid is at least one kind selected from the group consisting of lactic acid, acetic acid, propionic acid and butyric acid.

[18] A method for decreasing a ratio of bacteria belonging to the Firmicutes to bacteria belonging to the Bacteroidetes in the intestine, comprising administering an effective amount of an exopolysaccharide produced by *Leuconostoc mesenteroides* to a subject.

[19] The method of [18], wherein the *Leuconostoc mesenteroides* is *Leuconostoc mesenteroides* NTM048 strain deposited under accession number NITE BP-1519 or a mutant strain thereof.

[20] An exopolysaccharide produced by *Leuconostoc mesenteroides* for use in the prophylaxis or treatment of a metabolic disorder.

[21] The exopolysaccharide for use of [20], wherein the *Leuconostoc mesenteroides* is *Leuconostoc mesenteroides* NTM048 strain deposited under accession number NITE BP-1519 or a mutant strain thereof.

[22] The exopolysaccharide for use of [20] or [21], wherein the metabolic disorder is at least one kind selected from the group consisting of obesity, diabetes, impaired glucose tolerance, hyperinsulinemia, hyperlipemia, increase in adipose tissue and fatty liver.

[23] An exopolysaccharide produced by *Leuconostoc mesenteroides* for use in the amplification of the amount of short-chain fatty acid in the intestine.

[24] The exopolysaccharide for use of [23], wherein the *Leuconostoc mesenteroides* is *Leuconostoc mesenteroides* NTM048 strain deposited under accession number NITE BP-1519 or a mutant strain thereof.

[25] The exopolysaccharide for use of [23] or [24], wherein the short-chain fatty acid is at least one kind selected from the group consisting of lactic acid, acetic acid, propionic acid and butyric acid.

[26] An exopolysaccharide produced by *Leuconostoc mesenteroides* for use in decreasing a ratio of bacteria belonging to the Firmicutes to bacteria belonging to the Bacteroidetes in the intestine.

[27] The exopolysaccharide for use of [26], wherein the *Leuconostoc mesenteroides* is *Leuconostoc mesenteroides* NTM048 strain deposited under accession number NITE BP-1519 or a mutant strain thereof.

[28] Use of an exopolysaccharide produced by *Leuconostoc mesenteroides* in producing a prophylactic or therapeutic composition for a metabolic disorder.

[29] The use of [28], wherein the *Leuconostoc mesenteroides* is *Leuconostoc mesenteroides* NTM048 strain deposited under accession number NITE BP-1519 or a mutant strain thereof.

[30] The use of [28] or [29], wherein the metabolic disorder is at least one kind selected from the group consisting of obesity, diabetes, impaired glucose tolerance, hyperinsulinemia, hyperlipemia, increase in adipose tissue and fatty liver.

[31] Use of an exopolysaccharide produced by *Leuconostoc mesenteroides* in producing a composition for amplifying the amount of short-chain fatty acid in the intestine.

[32] The use of [31], wherein the *Leuconostoc mesenteroides* is *Leuconostoc mesenteroides* NTM048 strain deposited under accession number NITE BP-1519 or a mutant strain thereof.

[33] The use of [31] or [32], wherein the short-chain fatty acid is at least one kind selected from the group consisting of lactic acid, acetic acid, propionic acid and butyric acid.

[34] Use of an exopolysaccharide produced by *Leuconostoc mesenteroides* in producing a composition for decreasing a ratio of bacteria belonging to the Firmicutes to bacteria belonging to the Bacteroidetes in the intestine.

[35] The use of [34], wherein the *Leuconostoc mesenteroides* is *Leuconostoc mesenteroides* NTM048 strain deposited under accession number NITE BP-1519 or a mutant strain thereof.

Effect of the Invention

In the present invention, it was found that an exopolysaccharide produced by *Leuconostoc mesenteroides* has a suppressive action on body weight gain, a suppressive action on adipose tissue increase, a suppressive action on blood glucose level increase, an increasing action on the amount of short-chain fatty acid in the intestine, and a decreasing action on the ratio of bacteria belonging to the Firmicutes to bacteria belonging to the Bacteroidetes in the intestine, which are conventionally unknown physiological functions. The present invention provides, based on the functions, a prophylactic or therapeutic composition for a metabolic disorder, a composition for amplifying the amount of short-chain fatty acid in the intestine, or a composition for decreasing the ratio of bacteria belonging to the Firmicutes to bacteria belonging to the Bacteroidetes in the intestine, each comprising an exopolysaccharide produced by *Leuconostoc mesenteroides* as an active ingredient. The composition can be used in various fields such as pharmaceutical product, food, feed and the like. Therefore, the present invention is industrially extremely useful.

DESCRIPTION OF EMBODIMENTS

Figure 1:
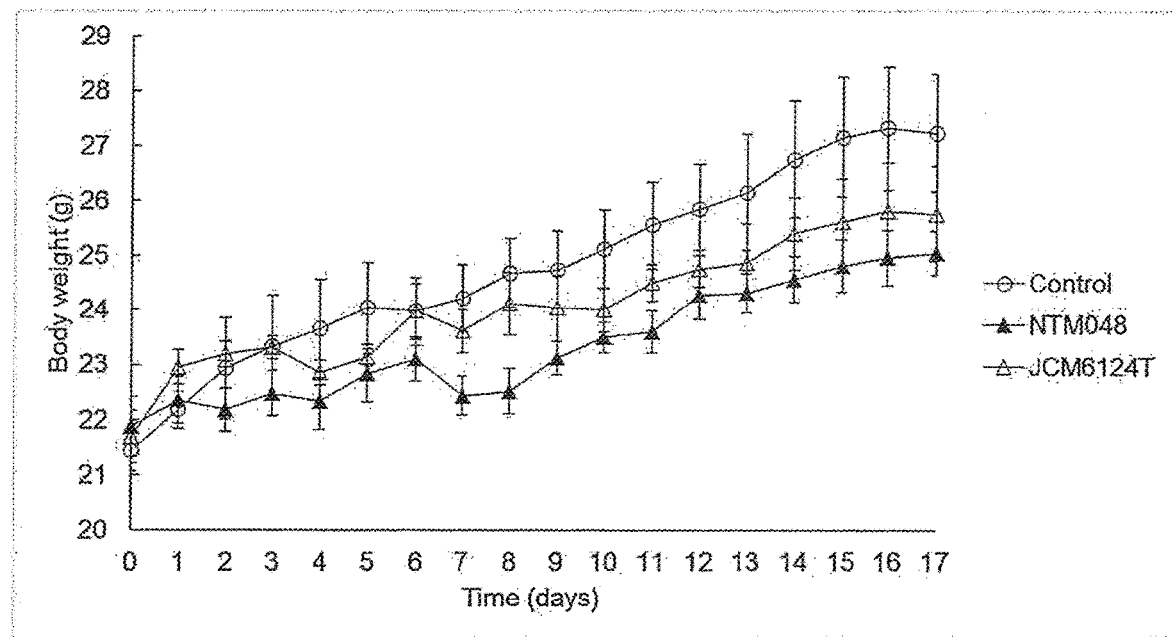
FIG. 1 shows the profile of the body weight of high-fat diet loaded mouse after ingesting EPS.

The present invention provides a prophylactic or therapeutic composition for a metabolic disorder, comprising an exopolysaccharide produced by *Leuconostoc mesenteroides* (preferably, *Leuconostoc mesenteroides* NTM048 strain deposited under accession number NITE BP-1519 or a mutant strain thereof) as an active ingredient, a composition for amplifying the amount of short-chain fatty acid in the intestine, or a composition for decreasing the ratio of bacteria belonging to the Firmicutes to bacteria belonging to the Bacteroidetes in the intestine.

In the present invention, exopolysaccharide (hereinafter the exopolysaccharide of the present invention) is a polysaccharide produced by *Leuconostoc mesenteroides* and can be classified into homopolysaccharide or heteropolysaccharide. Homopolysaccharide is constituted solely of a single type monosaccharide. Examples thereof include, but are not limited to, α-glucan, β-glucan, galactan and the like. Heteropolysaccharide is constituted of repeat units of two or more kinds of different monosaccharides. Examples of the kind of monosaccharide constituting the repeat units include, but are not limited to, glucose, fructose, galactose, rhamnose, acetylglucosamine, acetylgalactosamine, fucose, glucuronic acid, nonsugar substituents (e.g., acetyl group, glycerol etc.) and the like. The exopolysaccharide of the present invention is preferably a homopolysaccharide composed of glucose as a constituent sugar such as α-glucan having an α-1,6 bond as a main chain and an α-1,3 bond as a branched chain, or a homopolysaccharide having fructose as a constituent saccharide such as fructan having β-2,1 bond or fructan having β-2,6 bond. Furthermore, the constituent sugar may be modified by a functional group. The average molecular weight of exopolysaccharide obtained by culturing *Leuconostoc mesenteroides* and separating same can be determined by a known method. For example, a relative molecular weight determination method by GPC liquid chromatography or GFC liquid chromatography and the like can be used. While the molecular weight of the exopolysaccharide of the present invention is not particularly limited, it is preferably 30,000-50,000.

In the present invention, *Leuconostoc mesenteroides* that produces exopolysaccharide (hereinafter the *Leuconostoc mesenteroides* of the present invention) is not limited to a particular strain. Particularly, *Leuconostoc mesenteroides* NTM048 strain deposited under accession number NITE BP-1519 or a mutant strain thereof is preferable. The above-mentioned NTM048 strain was deposited on Jan. 25, 2013 at Incorporated Administrative Agency National Institute of Technology and Evaluation Patent Microorganisms Depositary, 2-5-8 Kazusakamatari, Kisarazu-shi, Chiba, Japan. In addition, the above-mentioned mutant strain is more preferably such a mutant that the exopolysaccharide produced by the above-mentioned mutant strain has a suppressive action on body weight gain, a suppressive action on adipose tissue increase, a suppressive action on increase in blood glucose level, an increasing action on the amount of short chain fatty acid in the intestine and a decreasing action on the ratio of bacteria belonging to the Firmicutes to bacteria belonging to the Bacteroidetes in the intestine, which are equal to or higher than those of an exopolysaccharide produced by NTM048 strain. Examples of a method of introducing mutation include, but are not limited to, a method by a chemical substance treatment such as a nitroso compound (nitrosoamine, nitrosoguanidine etc.), an alkylating agent (EMS; ethyl methanesulfonate), UV irradiation, radiation irradiation and the like. Whether the exopolysaccharide produced by the obtained mutant strain shows a suppressive action on body weight gain, a suppressive action on adipose tissue increase, a suppressive action on increase in blood glucose level, an increasing action on the amount of short chain fatty acid in the intestine and a decreasing action on the ratio of bacteria belonging to the Firmicutes to bacteria belonging to the Bacteroidetes in the intestine, which are equal to or higher than those of an exopolysaccharide produced by NTM048 strain can be detected by measuring the below-mentioned index of metabolic disorder for the exopolysaccharide produced by the mutant strain and comparing same with that formed for an exopolysaccharide produced by NTM048 strain.

The exopolysaccharide of the present invention can be produced by culturing the *Leuconostoc mesenteroides* of the present invention. The *Leuconostoc mesenteroides* of the present invention can be cultivated using a medium for lactic acid bacteria culture (solid medium, liquid medium etc.) such as MRS medium and the like.

The medium may contain various vitamins (vitamin A, vitamin B1, vitamin B2, vitamin B6, vitamin C, vitamin D, vitamin E etc., and derivatives thereof), various amino acids (including natural amino acid and synthetic amino acid), nucleic acid bases (purine, pyrimidine), inorganic salts ($MgSO_4$, $MnSO_4$, $FeSO_4$, $NaCl$ etc.) and the like as necessary.

The *Leuconostoc mesenteroides* of the present invention can be prepared by culturing at a culture temperature of 30-37° C., more preferably 30-35° C., for a culture period of 16 hr-3 days, more preferably 1-2 days, at pH 3-8, more preferably pH 4-7.

While a method of separating exopolysaccharide from a culture medium is not particularly limited as long as exopolysaccharide is obtained, a culture medium can be separated by centrifugation and the like into supernatant and cells, an acid (e.g., trichloroacetic acid, perchloric acid etc.) or an organic solvent (e.g., acetone, methanol, ethanol etc.) is added to the supernatant to remove proteins, alcohol (e.g., ethanol, isopropanol etc.) is further added to precipitate and recover exopolysaccharide. The precipitate may be further purified (e.g., dialysis etc.). The aforementioned separation method can be appropriately adjusted according to culture medium, culture conditions and the like.

As in the below-mentioned Examples, the exopolysaccharide of the present invention showed a suppressive action on body weight gain, a suppressive action on adipose tissue increase, a suppressive action on blood glucose level increase, an increasing action on the amount of short-chain fatty acid in the intestine, and a decreasing action on the ratio of bacteria belonging to the Firmicutes to bacteria belonging to the Bacteroidetes in the intestine. Therefore, the exopolysaccharide of the present invention can be used as a prophylactic or therapeutic composition for metabolic disorder or a composition for amplifying the amount of short-chain fatty acid in the intestine (hereinafter the composition of the present invention).

In the present invention, the "metabolic disorder" refers to abnormality in at least one metabolism selected from the group consisting of lipid metabolism, sugar metabolism and energy metabolism.

Abnormality in lipid metabolism refers to a state in which decomposition of lipids present in body tissues, blood, or lymphoid tissues is excessively suppressed, a state in which synthesis of lipid is excessively promoted, or a state in which lipids are excessively accumulated in body tissues such as adipose tissue due to inhibition of the lipid decomposition and promotion of lipid synthesis. As used herein, the "lipid" is neutral fat (triglyceride, diglyceride, monoglyceride), cholesterol (particularly, LDL cholesterol).

Abnormality in sugar metabolism refers to a state in which the fasting blood sugar level increases excessively and a state in which sugar metabolism after taking a meal is excessively suppressed. Furthermore, abnormality in sugar metabolism also includes impaired glucose tolerance. The "sugar" here means monosaccharide, disaccharide or polysaccharide.

The disorder of energy metabolism means the state of abnormal balance of ingested energy level and release energy level, or the state of unattainable control of the normal balance.

Examples of the "metabolic disorder" in the present invention specifically include obesity (adult obesity, infantile obesity), diabetes (e.g., type 1 diabetes, type 2 diabetes, gestational diabetes, diabetic complications (arteriosclerosis, diabetic retinopathy, diabetic nephropathy, diabetic neuropathy etc.) and the like), impaired glucose tolerance, hyperinsulinemia, hyperlipemia (e.g., hypercholesterolemia, hypertriglyceridemia, high LDL-cholesterolemia, low HDL-cholesterolemia), increase in adipose tissues (e.g., subcutaneous fat, intraperitoneal fat), fatty liver and the like. In addition, the "metabolic disorder" of the present invention may include a lifestyle-related disease. The "lifestyle-related disease" is a disease group for which life habits such as eating habit, exercise habit, rest, smoking, drinking and the like are involved in the onset and progression thereof, and includes nutrition ataxia, anorexia, gastric cancer, large intestine cancer, gout, hypertension, nephrolithiasis, myocardial infarction, angina pectoris, gastric ulcer, kidney disease, osteoporosis, periodontitis, alcoholic hepatitis, cirrhosis, liver cancer, lung cancer, bronchitis, emphysema, periodontal disease, cerebral apoplexy, cerebral infarction, aneurysm, overwork death, insomnia and the like.

As an index of the aforementioned metabolic disorder, the amount of short-chain fatty acid in the intestine can be used. As the short-chain fatty acid in the present invention, fatty acid having a carbon number of 6 or below can be mentioned. Examples of such short-chain fatty acid include lactic acid, acetic acid, propionic acid, butyric acid (more preferably, lactic acid, acetic acid and propionic acid) and the like, and these occupy an important part in daily energy use. The inventors previously clarified that short-chain fatty acid, which is a fermented product by enteric bacterium, directly regulates sympathetic nerve via fatty acid receptor GPR41. GPR41 is abundantly present in the sympathetic neuron aggregate called sympathetic ganglion, short-chain fatty acid activates sympathetic nerve via GPR41 and increases energy consumption. In addition, inventors have reported that short-chain fatty acid suppresses insulin signal via fatty acid receptor GPR43 of adipocyte, thereby suppressing glucose uptake, and consequently suppresses fat accumulation, and the decrease in insulin sensitivity of the whole body is suppressed by suppressing obesity due to fat accumulation. Therefore, the level of metabolic disorder and treatment effect can be evaluated by measuring the amount of short-chain fatty acid in the intestine. More specifically, when the amount of short-chain fatty acid in the intestine is higher than that before treatment of the metabolic disorder, the metabolic disorder can be judged to have been improved.

Alternatively, as an index of the metabolic disorder, the body weight, weight of subcutaneous or organ periphery fat and blood glucose level of an animal ingesting a high-fat diet can be used. The animal that ingests a high-fat diet is not limited as long as it is an animal exhibiting the properties. For example, as the aforementioned animal model, commercially available C57BL/6J mouse, KKAy mouse, NOD mouse, NSY mouse, TSOD mouse, ZDF/Crl-Leprfa rat, SDT/Jcl rat and the like can be mentioned. Therefore, the level of metabolic disorder and treatment effect can be evaluated by measuring the body weight, weight of subcutaneous or organ periphery fat and blood glucose level. More specifically, when the body weight, weight of subcutaneous or organ periphery fat and blood glucose level are lower than those before treatment of the metabolic disorder, the metabolic disorder can be judged to have been improved. On the other hand, when the body weight, weight of subcutaneous or organ periphery fat and blood glucose level are higher than those before treatment of the metabolic disorder, the metabolic disorder can be judged to have been aggravated.

Alternatively, as an index of the metabolic disorder, a ratio of bacteria belonging to the Firmicutes to bacteria belonging to the Bacteroidetes in the intestine can be used. There are not less than 100 trillion bacteria in the human intestine, and about 90% thereof are classified into Firmicutes and Bacteroidetes. Firmicutes are further classified into the classes of Bacilli, Clostridia, and Erysipelotrichia, and include bacteria belonging to the genera of *Bacillus, Alicyclobacillus, Listeria, Paenibacillus, Pasteuria, Planococcus, Sporolactobacillus, Staphylococcus, Lactobacillus, Pediococcus, Aerococcus, Carnobacterium, Enterococcus, Leuconostoc, Weissella, Streptococcus, Lactococcus, Clostridium, Eubacterium, Gracilibacter, Heliobacterium, Peptococcus, Peptostreptococcus, Ruminococcus, Syntrophomonas, Veilonella, Anaerococcus, Acidaminobacter, Anaerovorax, Anaerobranca, Aminobacterium, Carboxydocella, Sulfobacillus, Symbiobacterium, Acetoanaerobium, Halanaerobium, Caldicellulosiruptor, Erysipelothrix* and the like. Bacteroidetes are further classified into the classes of Bacteroidetes, Flavobacteria, and Sphingobacteria and includes bacteria belonging to the genera of *Bacteroides, Fusobacterium, Flavobacteria, Sphingobacterium* and the like.

It is known that bacteria belonging to the Firmicutes and bacteria belonging to the Bacteroidetes, which constitute the major part of the intestinal microflora, are related to obesity, obese individuals have many bacteria belonging to the Firmicutes and less bacteria belonging to the Bacteroidetes. Therefore, Firmicutes/Bacteroidetes obtained by analyzing the intestinal microflora can be used to evaluate the level of metabolic disorder and treatment effect. More specifically, when the ratio of bacteria belonging to the Firmicutes to bacteria belonging to the Bacteroidetes in the intestine is lower than that before treatment of the metabolic disorder, the metabolic disorder can be judged to have been improved.

The composition of the present invention can be used as, for example, a pharmaceutical product, a food, a feed, and the like, or by adding the agent to them.

When the composition of the present invention is used as a pharmaceutical product, the dosage form of the pharmaceutical product includes dispersion, granule, pill, soft capsule, hard capsules, tablet, chewable tablet, quick-disintegrating tablet, syrup, liquid, suspension, suppository, ointment, cream, gel, adhesive, inhalant, injection and the like. A preparation thereof is prepared according to a conventional method.

Examples of the additives that can be used for formulating include animal and plant oils such as soybean oil, safflower oil, olive oil, germ oil, sunflower oil, beef fat, sardine oil and the like, polyalcohols such as polyethylene glycol, propylene glycol, glycerol, sorbitol and the like, surfactants such as sorbitan ester of fatty acid, sucrose ester of fatty acid, glycerin fatty acid ester, polyglycerol ester of fatty acid and the like, excipients such as purified water, lactose, starch, crystalline cellulose, D-mannitol, lecithin, gum arabic, sorbitol solution, carbohydrate solution and the like, sweetener, colorant, pH adjuster, flavor and the like. A liquid preparation may be dissolved or suspended in water or other suitable medium when in use. Also, tablet and granules may be coated by a well-known method.

For administration in the form of an injection, intravenous, intraperitoneal, intramuscular, subcutaneous, transdermal, intraarticular, intrasynovial, intrathecal, intraperiosteum, sublingual, oral administrations and the like are preferable, and intravenous administration or intraperitoneal administration is particularly preferable. The intravenous administration may be any of drip administration and bolus administration.

When the composition of the present invention is used as a food or a food additive, the form of the food is not particularly limited as long as it permits oral ingestion, such as solution, suspension, powder, solid formed article and the like. Specific examples include supplements (powder, granule, soft capsule, hard capsule, tablet, chewable tablet, quick-integrating tablet, syrup, liquid etc.), drinks (carbonic acid drinks, lactic acid drinks, sport drinks, fruit juice drinks, vegetable drinks, soymilk beverage, coffee drinks, tea drinks, powder drinks, concentrated drinks, nutrition drinks, alcohol drinks etc.), confectionery (gummy candy, jelly, gum, chocolate, cookie, candy, caramel, Japanese confectionery, snack etc.), instant food (instant noodles, retort food, can, microwavable foods, instant soup, miso soups, freeze-dried food etc.), oil, fats and oils food (mayonnaise, dressing, butter, cream, margarine etc.), wheat powder products (bread, pasta, noodle, cake mix, bread crumb etc.), seasoning (sauce, tomato processing seasoning, flavor seasoning, cooking mixture, soup etc.), processed meat products (meat ham, sausage etc.).

The above-mentioned foods can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, *agaricus* and the like.

When the composition of the present invention is used as a feed or a feed additive, the feed is, for example, pet food, stock raising or aquaculture feed additive and the like.

As the subject to be administered with or that ingests the composition of the present invention, human and animals other than human (e.g., dog, cat, mouse, rat, hamster, guinea pig, rabbit, swine, bovine, chicken, parakeet, hill myna, goat, horse, sheep, monkey etc.) can be mentioned.

While the dose or ingestion amount of the composition of the present invention varies depending on the subject of administration or ingestion, target disease, symptom, administration or ingestion route and the like, for example, a daily dose or ingestion amount of the exopolysaccharide contained in the composition of the present invention is generally 0.5 µg-30 g, preferably 5 µg-10 g, more preferably 50 µg-5 g, which can be administered or ingested orally or parenterally. Plural divided portions may be administered or ingested per day. When the condition is particularly serious, the dose or ingestion amount may be increased according to the symptom.

The present invention is explained in more detail in the following by referring to Examples. The Examples are mere exemplifications of the present invention and do not limit the scope of the present invention in any manner.

EXAMPLES

Medium, Strain
medium: MRS medium (manufactured by Difco)
strain: NTM048 strain [isolated from pea (accession No.: NITE BP-1519, date of deposition: Jan. 25, 2013)], JCM6124 strain (*Leuconostoc mesenteroides* subsp. *mesenteroides*) [purchased from RIKEN, Tsukuba, BioResource Center, Japan Collection of Microorganism (JCM)]

Production and Purification Method of Exopolysaccharide (EPS)

EPS was extracted according to the production and purification method for EPS of *L. mesenteroides* strain (Sarwat, Ul Qader, Aman, &Ahmed, 2008).

*Leuconostoc mesenteroides* culture medium (500 µL) cultured overnight was added to EPS production medium (50 mL, composition: 15% sucrose, 0.5% bacto-peptone, 0.5% yeast extract, 1.5% $K_2HPO_4$, 0.001% $MnCl_2 \cdot H_2O$, 0.001% NaCl, 0.005% $CaCl_2$), cultured at 30° C. for 24 hr and centrifuged, and bacteria were removed. Cold ethanol in the same amount as the supernatant was added to allow for precipitation, and the mixture was shaken vigorously and centrifuged at 10,000 rpm for 15 min, and the supernatant was removed. This step was repeated twice. The precipitated EPS was dried on calcium chloride for 12 hr. To remove impurity, EPS precipitate was dissolved in distilled water, and cold ethanol in the same amount as the suspension was added again to allow for precipitation. This step was repeated twice. The precipitated EPS was dried on calcium chloride for 12 hr. The EPS was used for the measurement of the effect in high-fat diet mouse. EPS produced from the NTM048 strain is indicated as "NTM048-EPS", and EPS produced from the JCM6124T strain is indicated as "JCM6124T-EPS".

Example 1: Effect of EPS in High-Fat Diet Mouse

Figure 2:
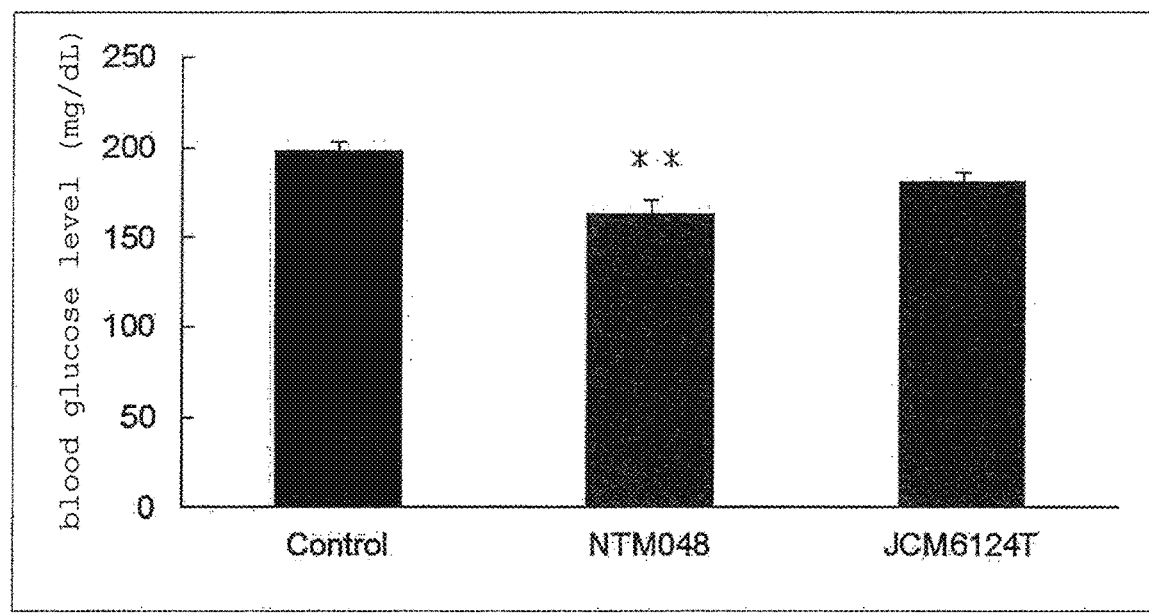
FIG. 2 shows the blood glucose level of high-fat diet loaded mouse after ingesting EPS. **: P<0.01
Figure 3:
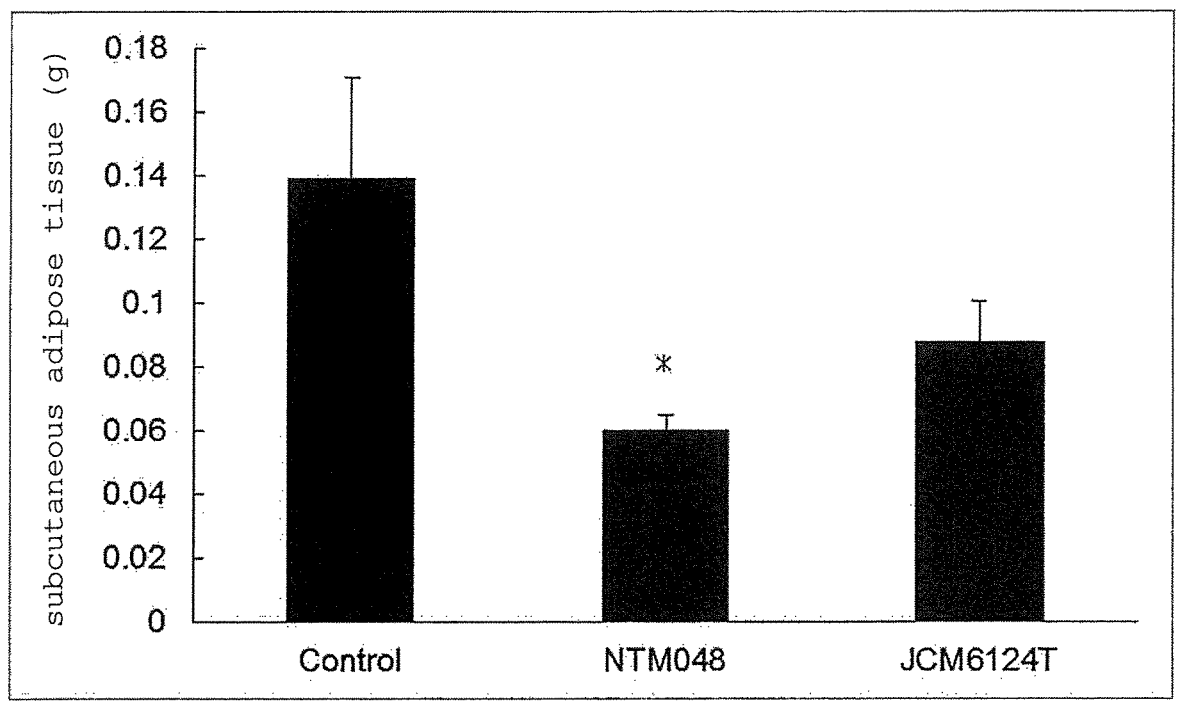
FIG. 3 shows the weight of subcutaneous adipose tissue of high-fat diet loaded mouse after ingesting EPS. *: P<0.05
Figure 4:
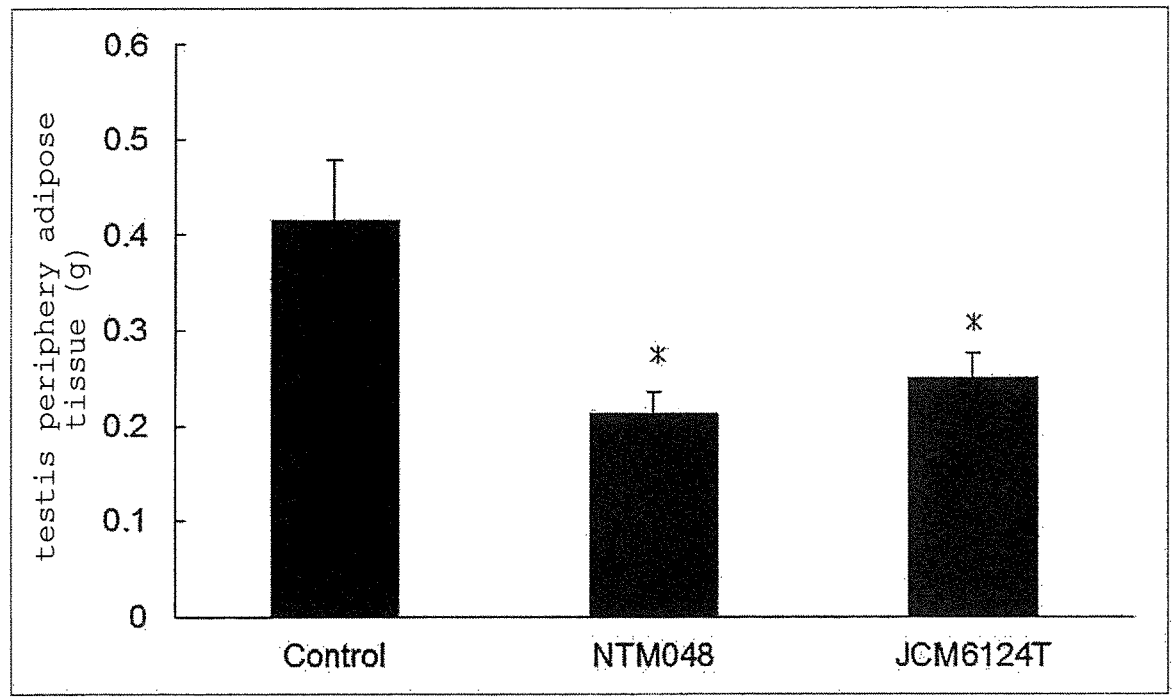
FIG. 4 shows the weight of testis periphery adipose tissue of high-fat diet loaded mouse after ingesting EPS. *: P<0.05
Figure 5:
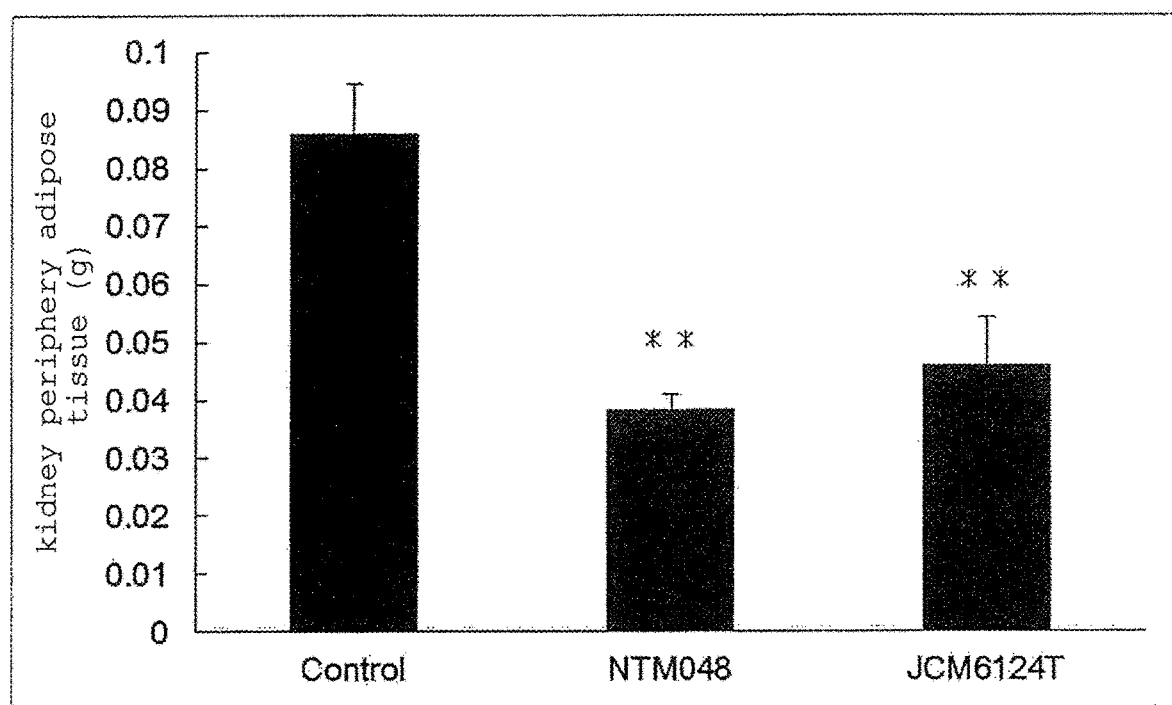
FIG. 5 shows the weight of kidney periphery adipose tissue of high-fat diet loaded mouse after ingesting EPS. P<0.01

The effects of *Leuconostoc mesenteroides*-derived EPS on the body weight, adipose tissue and blood glucose level of mouse fed with a high-fat diet were evaluated. C57BL/6J mice (male, 6-week-old, purchased from CLEA Japan, Inc. and separately bred) were preliminarily bred for 2 weeks on a commercially available normal breeding feed (ND), divided into 3 groups, and respectively bred for 17 days on a high-fat feed (HFD) as a basic feed and blended with Cellulose to 10% (feed for Control group), the basic feed blended with NTM048-EPS to 5% and Cellulose to 5% (feed for NTM048 group), and the basic feed blended with JCM6124T-EPS to 5% and Cellulose to 5% (feed for JCM6124T group). The profile of the body weight of C57BL/6J mice in each group is shown in FIG. 1. The body weight gain was suppressed more in the NTM048 group and JCM6124T group than the Control group. On day 17 of breeding, the blood glucose level was measured, the C57BL/6J mice in each group were autopsied, and subcutaneous adipose tissue, testis periphery adipose tissue and kidney periphery adipose tissue were respectively measured. The blood glucose level of C57BL/6J mice in each group is shown in FIG. 2. A significant decrease in the blood glucose level was found in the NTM048 group than in the Control group. In addition, a blood glucose level-decreasing tendency was also found in the JCM6124T group as compared to the Control group. In addition, a significant decrease in the subcutaneous adipose tissue weight (FIG. 3) and testis periphery adipose tissue weight (FIG. 4) was found more in the NTM048 group than the Control group, and a decreasing tendency was also found in the JCM6124T group as compared to the Control group. As for the kidney periphery adipose tissue weight (FIG. 5), significantly lower results were obtained both in the NTM048 group and the JCM6124T group than in the Control group.

Example 2: Measurement of Short-Chain Fatty Acid in Feces of High-Fat Diet Mouse The short-chain fatty acid produced in the feces of mice fed with *Leuconostoc mesenteroides*-derived EPS and high-fat diet was measured. In the same manner as in Example 1, C57BL/6J mice were preliminarily bred for 2 weeks on a commercially available normal breeding feed (ND), divided into 3 groups, and respectively bred for 17 days on a high-fat feed (HFD) as a basic feed and blended with Cellulose to 10% (feed for Control group), the basic feed blended with NTM048-EPS to 10% (feed for NTM048 group), and the basic feed blended with JCM6124T-EPS to 10% (feed for JCM6124T group). The feces on day 17 of breeding was collected, and short-chain fatty acid (SCFAs: lactic acid, acetic acid, propionic acid, butyric acid) was measured. The short-chain fatty acid (SCFAs) in the feces of C57BL/6J mice was measured using "labeling reagent for long chain, short-chain fatty acid analysis by high performance liquid chromatography" manufactured by YMC. The collected mouse feces (0.1 g) was suspended in distilled water (0.2 mL) and 12% perchloric acid (0.03 mL), the suspension was centrifuged (14000 rpm, 1 min), and the upper layer (100 µL) was collected. The layer was reacted with 2-nitrophenylhydrazine hydrochloride (2-NPH/HCL) in the presence of 1-ethyl-3-(3-dimetylaminopropyl) carbodiimide hydrochloride (1-EDC/HCL), extracted with hexane and ether, and the obtained sample was measured by high-performance liquid chromatography (HPLC) apparatus. The HPLC conditions were as described below.

HPLC Conditions
measurement apparatus: SCL-10Av and SPD-20A (Shimadzu Seisakusho, Kyoto, Japan)
column: YMC-Pack FA (column exclusively for fatty acid analysis)
acetonitrile:methanol:water=22:8:70
flow rate: 1.0 ml/min
analysis time: 30 min
detection sensitivity: UV at 400 nm
temperature: 50° C.

Figure 6:
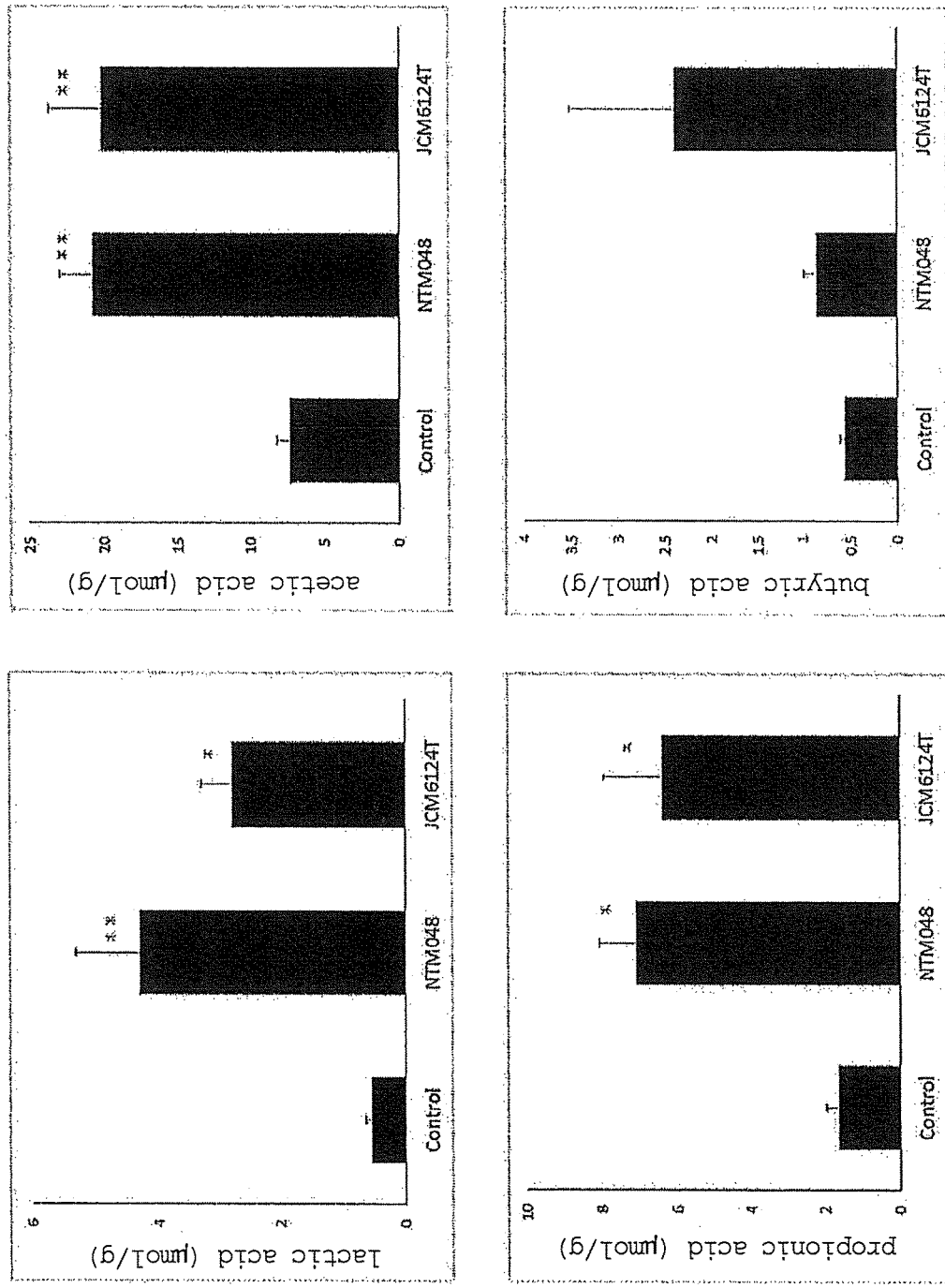
FIG. 6 shows the amount of short-chain fatty acid in the feces of high-fat diet loaded mouse after ingesting EPS. *: P<0.05, **: P<0.01

The measurement results of the short-chain fatty acid (SCFAs: lactic acid, acetic acid, propionic acid, butyric acid) in the feces of C57BL/6J mouse are shown in FIG. 6. It was found that the amount of the short-chain fatty acid was higher in the NTM048 group and JCM6124T group than in the Control group.

Figure 7:
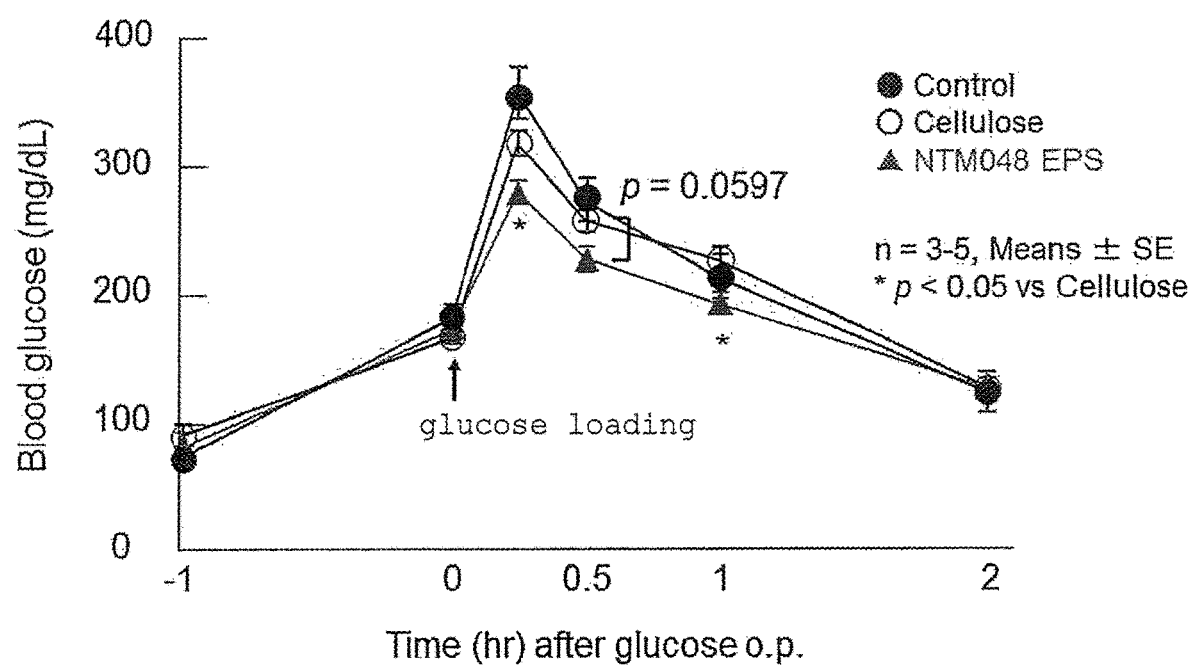
FIG. 7 shows the blood glucose level of mouse after ingesting EPS and loaded with glucose.

Example 3: Effect of EPS on Postprandial Elevated Blood Glucose Level in Mouse The effect of *Leuconostoc mesenteroides*-derived EPS on postprandial hyperglycemia was evaluated. C57BL/6J mice (male, 6-week-old, purchased from CLEA Japan, Inc. and separately bred) were preliminarily bred on a commercially available normal breeding feed (ND), divided into 3 groups, fasted for 24 hr, and respectively given a feed without Cellulose as a basic feed (0.1 g for Control group), the basic feed (0.1 g) blended with Cellulose (0.1 g) (feed 0.2 g for Cellulose group), and the basic feed (0.1 g) blended with NTM048-EPS (0.1 g) (feed 0.2 g for NTM048 group). Thereafter, a glucose solution (300 mg/mL) was oral administered at 100 µL/20 g body weight, and the blood glucose level was measured with time (0, 15, 30, 60, 120 min after glucose loading). The profile of the blood glucose level of C57BL/6J mouse in each group is shown in FIG. 7. The results showing lower blood glucose level were obtained in the NTM048 group than in the Cellulose group at 15 min and 60 min after glucose administration.

Example 4: Effect of EPS in High-Fat Diet Mouse

Figure 8:
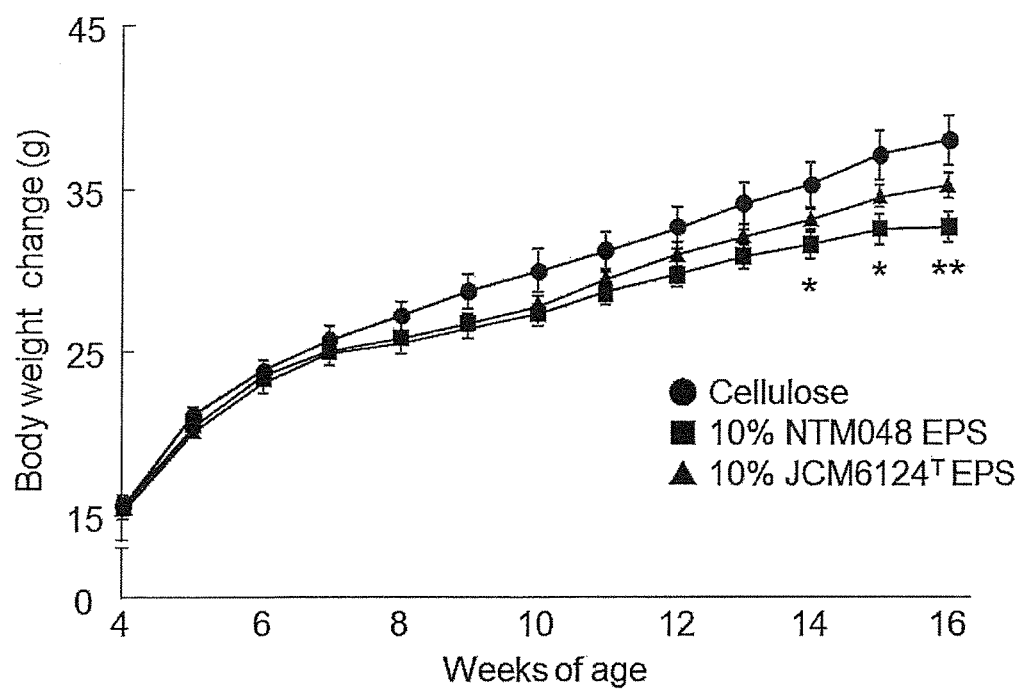
FIG. 8 shows the profile of the body weight of high-fat diet loaded mouse after ingesting EPS for a long term.

C57BL/6J mice (male, 6-week-old, purchased from CLEA Japan, Inc. and separately bred) were preliminarily bred for 2 weeks on a commercially available normal breeding feed (ND), divided into 3 groups, and respectively bred for 16 weeks on a high-fat feed (HFD) as a basic feed and blended with Cellulose to 10% (feed for Control group), the basic feed blended with NTM048-EPS to 10% (feed for NTM048 group), and the basic feed blended with JCM6124T-EPS to 10% (feed for JCM6124T group). Similar to Example 1, the profile of the body weight of C57BL/6J mice in each group is shown in FIG. 8. The body weight gain was suppressed more in the NTM048 group and JCM6124T group than in the Control group.

Figure 9:
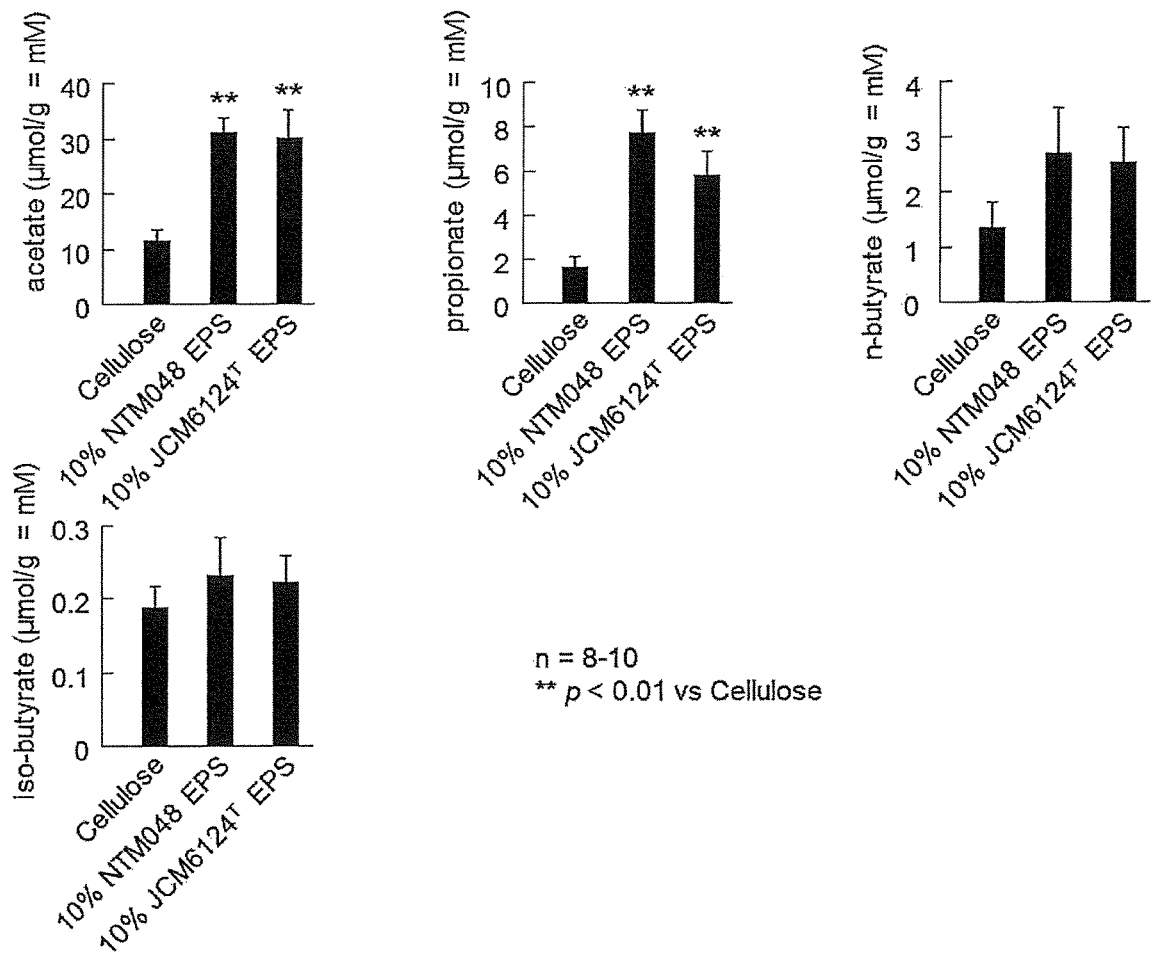
FIG. 9 shows the amount of short-chain fatty acid in the feces of high-fat diet loaded mouse after ingesting EPS for a long term.

In addition, the feces on week 16 of breeding was collected, and short-chain fatty acid (SCFA5: acetic acid, propionic acid, butyric acid) was measured in the same manner as in Example 2. The measurement results of the short-chain fatty acid (SCFAs: acetic acid, propionic acid, butyric acid) in the feces of C57BL/6J mouse are shown in FIG. 9. It was found that the amount of the short-chain fatty acid was higher in the NTM048 group and JCM6124T group than in the Control group.

Figure 10:
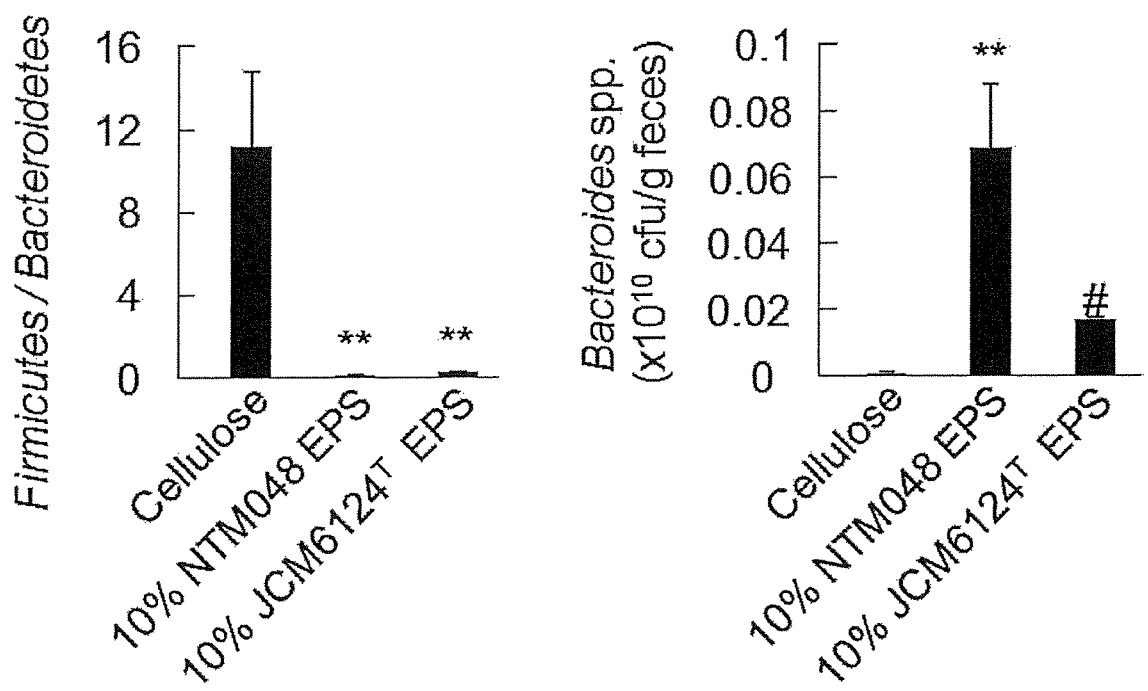
FIG. 10 shows Firmicutes/Bacteroidetes in the feces of high-fat diet loaded mouse after ingesting EPS for a long term.

Furthermore, the bacterial flora in the feces collected on week 16 of breeding was analyzed. DNA was extracted and purified from the feces, and real-time PCR was performed using 5'-CRAACAGGATTAGATACCCT-3' (SEQ ID NO: 1) and 5'-GGTAAGGTTCCTCGCGTAT-3' (SEQ ID NO: 2) as common primers for the measurement of the bacteria belonging to Bacteroidetes, and 5'-GGAGYATGTGGTT-TAATTCGAAGCA-3' (SEQ ID NO: 3) and 5'-AGCTGAC-GACAACCATGCAC-3' (SEQ ID NO: 4) as common primers for the measurement of the bacteria belonging to the Firmicutes, and the ratio of the bacteria belonging to the Firmicutes to the bacteria belonging to the Bacteroidetes (Firmicutes/Bacteroidetes) was measured (FIG. 10). The Firmicutes/Bacteroidetes decreased more in the NTM048 group and JCM6124T group than in the Control group.

The above results reveal that an exopolysaccharide produced by *Leuconostoc mesenteroides* has a suppressive action on body weight gain, a suppressive action on adipose tissue increase, a suppressive action on increase in blood glucose level, an increasing action on the amount of short chain fatty acid in the intestine and a decreasing action on the ratio of bacteria belonging to the Firmicutes to bacteria belonging to the Bacteroidetes in the intestine. Particularly, an exopolysaccharide produced by NTM048 strain was shown to have a strong metabolic disorder-improving effect.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

INDUSTRIAL APPLICABILITY

In the present invention, it has been clarified that exopolysaccharides produced by *Leuconostoc mesenteroides* have a suppressive action on body weight gain, a suppressive action on adipose tissue increase, a suppressive action on blood glucose level increase, an increasing action on the amount of short-chain fatty acid in the intestine, and a decreasing action on the ratio of bacteria belonging to the Firmicutes to bacteria belonging to the Bacteroidetes in the intestine, each of which is conventionally unknown. A prophylactic or therapeutic composition for a metabolic disorder, comprising an exopolysaccharide produced by *Leuconostoc mesenteroides* as an active ingredient, a composition for amplifying the amount of short-chain fatty acid in the intestine, or a composition for decreasing a ratio of bacteria belonging to the Firmicutes to bacteria belonging to the Bacteroidetes in the intestine, which are produced by *Leuconostoc mesenteroides*, are applicable to various fields such as pharmaceutical product, food, feed and the like and the present invention is industrially extremely useful.

This application is based on a patent application No. 2016-032889 (filing date: Feb. 24, 2016) and a patent application No. 2016-134997 (filing date: Jul. 7, 2016) filed in Japan, the contents of which are incorporated in full herein.

The invention claimed is:

1. A method for preventing or treating a metabolic disorder, comprising administering an effective amount of an exopolysaccharide produced by *Leuconostoc mesenteroides* to a subject,
wherein the *Leuconostoc mesenteroides* is *Leuconostoc mesenteroides* NTM048 strain deposited under accession number NITE BP-1519, and
wherein the metabolic disorder is at least one kind selected from the group consisting of obesity, type 2 diabetes, gestational diabetes, diabetic complications, impaired glucose tolerance, hyperinsulinemia, hyperlipemia, increase in adipose tissue, and fatty liver,
thereby preventing or treating the metabolic disorder in the subject.

2. A method for amplifying the amount of short-chain fatty acid in the intestine, comprising administering an effective amount of an exopolysaccharide produced by *Leuconostoc mesenteroides* to a subject, wherein the *Leuconostoc mesenteroides* is *Leuconostoc mesenteroides* NTM048 strain deposited under accession number NITE BP-1519, thereby amplifying the amount of short-chain fatty acid in the intestine of the subject.

3. A method for decreasing a ratio of bacteria belonging to the Firmicutes to bacteria belonging to the Bacteroidetes in the intestine, comprising administering an effective amount of an exopolysaccharide produced by *Leuconostoc mesenteroides* to a subject, wherein the *Leuconostoc mesenteroides* is *Leuconostoc mesenteroides* NTM048 strain deposited under accession number NITE BP-1519, thereby decreasing the ratio of bacteria belonging to the Firmicutes to bacteria belonging to the Bacteroidetes in the intestine of the subject.

4. The method according to claim 2, wherein the short-chain fatty acid is at least one kind selected from the group consisting of lactic acid, acetic acid, propionic acid and butyric acid.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
craacaggat tagataccct                                              20

<210> SEQ ID NO 2
<211> LENGTH: 19
<212> TYPE: DNA
<213> ORGANISM: Artificial Sequence
<220> FEATURE:
<223> OTHER INFORMATION: primer
```

```
<400> SEQUENCE: 2
ggtaaggttc ctcgcgtat                                                    19

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
ggagyatgtg gtttaattcg aagca                                             25

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
agctgacgac aaccatgcac                                                   20
```